US 8,887,558 B2

(12) United States Patent
Kawazoe (10) Patent No.: US 8,887,558 B2
(45) Date of Patent: Nov. 18, 2014

(54) HARDNESS TESTER AND TESTING METHOD (75) Inventor: Masaru Kawazoe, Yamato (JP)

(73) Assignee: Mitutoyo Corporation, Kanagawa (JP)

(*) Notice: Subject to any disclaimer, the term of this patent is extended or adjusted under 35 U.S.C. 154(b) by 241 days.

(21) Appl. No.: 13/472,745

(22) Filed: May 16, 2012

(65) Prior Publication Data
US 2013/0008241 A1 Jan. 10, 2013

(30) Foreign Application Priority Data

Jul. 5, 2011 (JP) ................................ 2011-148741

(51) Int. Cl.
G01N 3/48 (2006.01)
G01N 3/42 (2006.01)
G01N 3/06 (2006.01)

(52) U.S. Cl.
CPC .......... *G01N 3/42* (2013.01); *G01N 2203/0647* (2013.01); *G01N 3/068* (2013.01)
USPC .................................................. 73/81; 850/1

(58) Field of Classification Search
CPC ............. G01N 3/40; G01N 3/42; G01N 3/44; G01N 2203/0098; G01N 2203/0286
USPC ............... 73/78, 81, 83, 105; 850/1, 2, 3, 5, 6
See application file for complete search history.

(56) References Cited

U.S. PATENT DOCUMENTS

| 5,146,779 A * | 9/1992 | Sugimoto et al. ................. 73/81 |
| 5,486,924 A * | 1/1996 | Lacey ............................ 356/507 |
| 6,155,104 A * | 12/2000 | Suresh et al. ...................... 73/81 |
| 6,301,956 B1 * | 10/2001 | Fujita et al. ........................ 73/82 |
| 2003/0070475 A1 * | 4/2003 | Nagashima et al. ............... 73/81 |
| 2005/0265593 A1 * | 12/2005 | Hauck et al. .................. 382/141 |
| 2006/0288763 A1 * | 12/2006 | Tsujii et al. ....................... 73/81 |
| 2011/0178728 A1 * | 7/2011 | Sawa ............................... 702/41 |

FOREIGN PATENT DOCUMENTS

JP 2011-2247 A 1/2011

* cited by examiner

Primary Examiner — Hezron E Williams
Assistant Examiner — Marrit Eyassu
(74) Attorney, Agent, or Firm — Greenblum & Bernstein, P.L.C.

(57) ABSTRACT

A hardness tester and testing method including a focuser, an image capturer, a test position setter, a focus position memory, an indentation creator, an image capture controller, and a measurer. The focuser focuses on the surface of the specimen. The image capturer captures an image of the surface of the specimen. The test position setter sets a test position at which the indentation is formed. The focus position memory measures a focus position, then associates the focus position with a test position within a predetermined range and stores the information in a memory. The indentation creator forms the indentation at the test position with the indenter. The image capture controller displaces the specimen, then captures an image of the formed indentation through the first field lens. The measurer measures the hardness of the specimen based on the indentation whose image has been captured.

3 Claims, 9 Drawing Sheets

| Test position (X, Y) | Focus position (Z) |
|---|---|
| P1 ( X1 , Y1 ) | Z1 |
| P2 ( X2 , Y2 ) | |
| P3 ( X3 , Y3 ) | |
| P4 ( X4 , Y4 ) | |
| ⋮ | ⋮ |
| Pn ( Xn , Yn ) | Zn |
| ⋮ | ⋮ |

RELATED ART

HARDNESS TESTER AND TESTING METHOD

CROSS-REFERENCE TO RELATED APPLICATIONS

The present application claims priority under 35 U.S.C. §119 of Japanese Application No. 2011-148741, filed on Jul. 5, 2011, the disclosure of which is expressly incorporated by reference herein in its entirety.

BACKGROUND OF THE INVENTION

1. Field of the Invention

The present invention relates to a hardness tester and a hardness testing method.

2. Description of Related Art

Conventionally, for each kind of hardness tester, such as a Brinell hardness tester, a Vickers hardness tester, a Knoop hardness tester, and the like, hardness of a specimen has been measured based on dimensions of an indentation formed in a surface of the specimen. For example, in the Vickers hardness tester, an indenter with a four-sided pyramid-shaped tip is pressed onto a surface of the specimen, then the length of diagonal lines in the indentation formed on the specimen is measured with an optical microscope and the like. Then, based on the measured length of the diagonal lines in the indentation, hardness is calculated. Also, in order not to generate measurement errors in measuring the dimensions of the indentation, a user must perform focusing on the surface of the specimen on which the indentation has been formed.

A known example for the hardness tester in which focusing is performed designates a plurality of focus adjustment positions on the specimen on which the indentation has been formed. An image capturer is then operated so as to focus on the designated focus adjustment positions and an image of the indentation is captured. A degree of focus for the indentation in the designated focus adjustment position is calculated, then displayed on a monitor. Focus adjustment can thus be performed favorably (see, for example, Japanese Patent Laid-open Publication No. 2011-2247).

Figure 6:
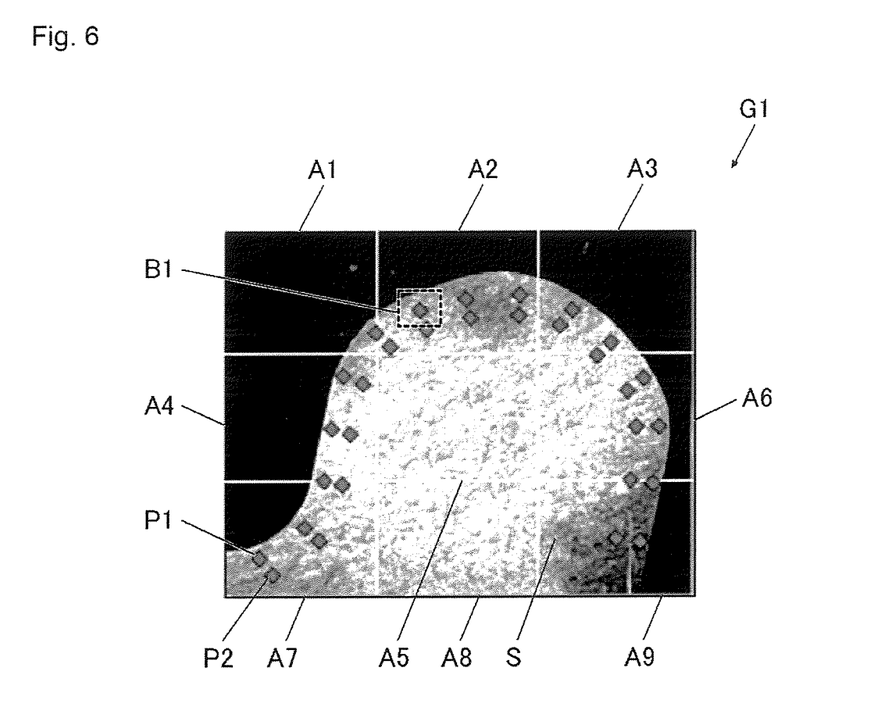
FIG. 6 illustrates an example of a broad range image of a specimen.

In the conventional hardness tester, during programming of a test position, a broad range image of a specimen S must be obtained in order to verify at which location on the specimen S the hardness test will be performed. For example, as shown in FIG. 6, by combining a plurality of images A1-A9 captured by displacing the specimen S in a horizontal direction, a broad range image G1 is obtained. Then, the broad range image G1 obtained is used to perform hardness testing.

Figure 8:
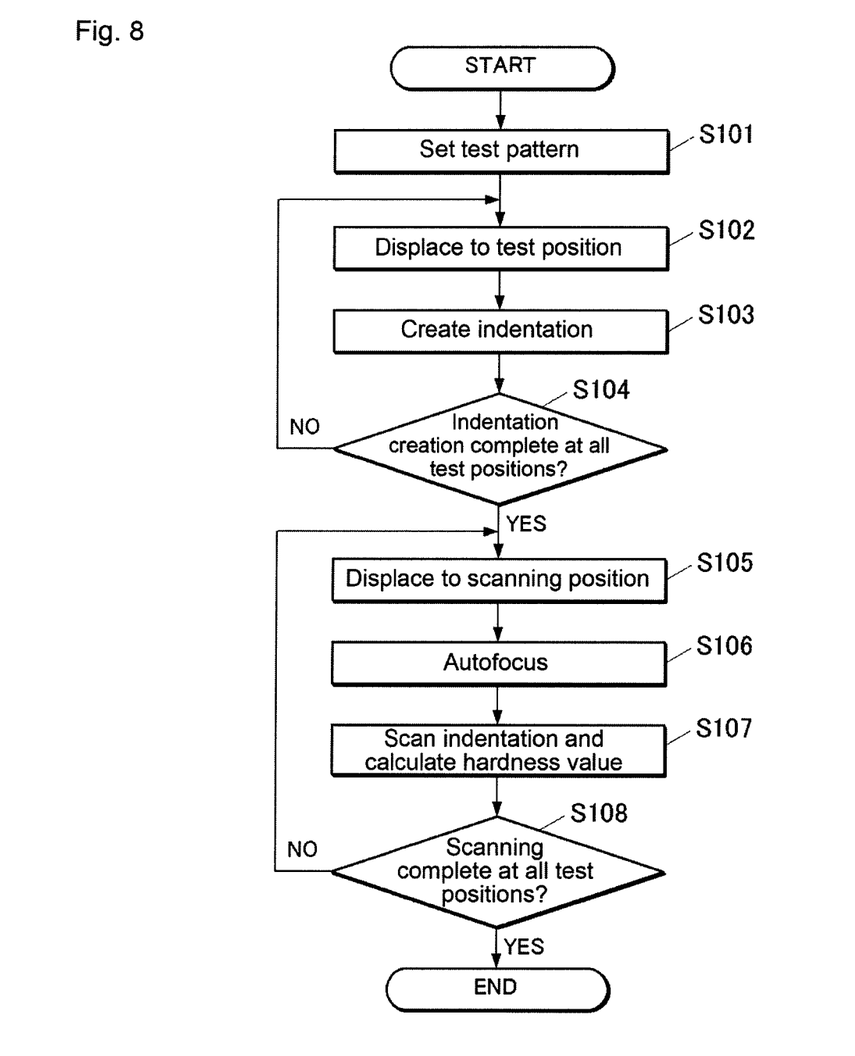
FIG. 8 is a flowchart illustrating an operation after obtaining the broad range image of the specimen in the hardness tester according to the conventional art.
Figure 9:
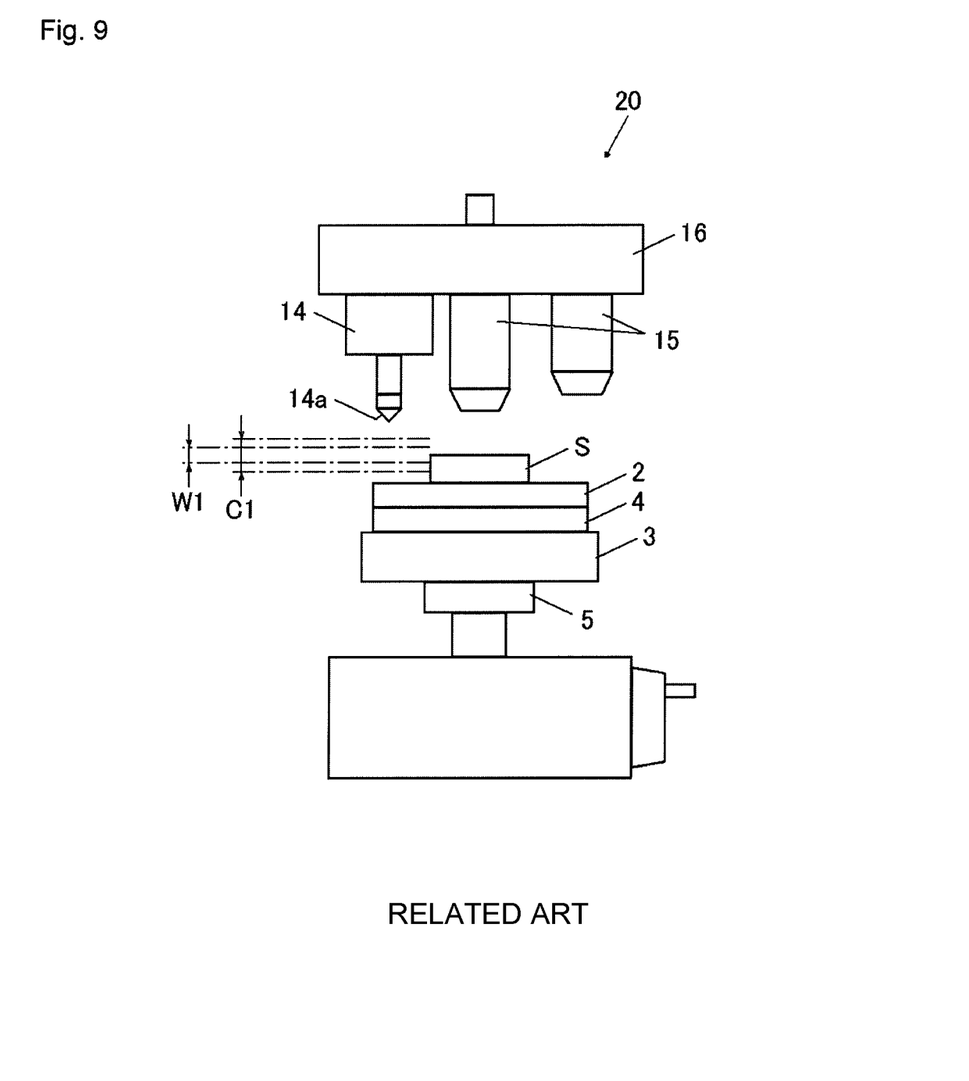
FIG. 9 is a schematic diagram illustrating a tester main body of a hardness tester according to the conventional art.

Herein, a process after the broad range image G1 is obtained in the conventional hardness tester is described with reference to the flowchart of FIG. 8 and to the schematic diagram of FIG. 9 illustrating a tester main body 20 of a hardness tester. First, a test pattern is set with respect to the obtained broad range image G1 (step S101). Herein, the setting of a test pattern refers to setting test conditions, a test start point, number of rows and columns, pitch, and the like. By setting the test pattern, as shown in FIG. 6, programming of test positions P1, P2, . . . is performed.

When the test pattern has been set, the hardness test begins automatically. The specimen S (specimen stage 2) is displaced so as to position the predetermined test positions (in the first cycle, the test start point) that opposes an indenter 14a (step S102). An indentation is then created at the test position (step S103).

Next, whether or not indentations have been created for all of the programmed test positions is determined (step S104). When indentation has not been performed for all of the test positions (that is, when it is determined that at least one test position has not had an indentation created thereat) (step S104: NO), the process moves to step S102 and displaces the specimen S so as to position the next test position opposite the indenter 14a. Meanwhile, when indentation is determined to have been performed for all test positions (step S104: YES), the specimen S is displaced so as to position predetermined scanning positions (positions where indentation has been performed) opposite a field lens 15 used for indentation scanning (step S105). An autofocus process is then performed to focus on the scanning position (step S106).

When the autofocus process is performed, an indentation is scanned in the scanning position, then a hardness value for the specimen S is calculated based on the dimensions of the scanned indentation (step S107).

Finally, whether or not the indentation has been scanned in all scanning positions is determined (step S108). When the indentation has not been scanned in all scanning positions (that is, when it is determined that the indentation has not been scanned in at least one scanning position) (step S108: NO), the process moves to step S105 and displaces the specimen S so as to position the next scanning position opposite the indenter 14a. Meanwhile, when the indentation is determined to be scanned at all scanning positions (step S108: YES), the process ends.

In this way, the broad range image G1 is obtained and test positions are programmed using the obtained broad range image G1, thereby enabling a hardness test to be performed in the conventional hardness tester.

SUMMARY OF THE INVENTION

However, in the conventional hardness tester, when obtaining the broad range image G1, an image having a high field of view (for example, A1-A9 in FIG. 6) is obtained by using a low power field lens. However, when a low power field lens is used, a field depth C1 is deep. For example, as shown in FIG. 9, the field depth C1 may exceed an allowed range W1 for height of the specimen S during indentation. Accordingly, there is a risk that the field depth C1 may be positioned exceeding the allowed range W1 for height of the specimen S. Also, when an indentation is created in such a state, an unfavorable circumstance arises in which measurement errors are produced during indentation scanning.

Meanwhile, when an image is obtained using a high power field lens, the field depth is shallow compared to the low power field lens and does not exceed the allowed range W1 for height of the specimen S. Accordingly, there is an advantage that accuracy is high for positioning the height of the specimen S. However, as shown in FIG. 6, because the field of view for an obtained image B1 is narrow, an extremely large number of images must be captured in order to obtain the broad range image G1, incurring a great deal of time and effort.

The present invention has as its advantage to provide a hardness tester and a hardness testing method capable of positioning a specimen at an appropriate height and of shortening the execution time of a hardness test.

One aspect of the present invention is conceived to achieve this advantage. A hardness tester measures hardness of a specimen by loading a predetermined testing force from an indenter on a surface of a specimen placed on a specimen stage to form an indentation, then measuring dimensions of the indentation. The hardness tester includes a focuser, an image capturer, a test position setter, a focus position memory controller, an indentation creator, an image capture controller, and a measurer. The focuser focuses on the surface of the specimen by changing a relative distance between a specimen stage and one of a first field lens and a second field lens having a magnification power less than the first field lens. The image capturer captures an image of the surface of the specimen through one of the first field lens and the second field lens. The test position setter sets a test position at which the indentation is formed based on image information for the surface of the specimen captured by the image capturer through the second field lens. The focus position memory controller measures a focus position through the first field lens at a predetermined test position among the test positions set by the test position setter, then associates the measured focus position with a test position within a predetermined range and stores the information in a memory. The indentation creator forms the indentation at the test position with the indenter. The image capture controller obtains the focus position associated with the test position from the memory, then displaces the specimen based on the obtained focus position and the test position. Thereafter, the image capture controller captures an image of the indentation formed by the indentation creator with the image capturer through the first field lens. The measurer measures the hardness of the specimen based on the indentation whose image has been captured by the control of the image capture controller.

Another aspect of the present invention is the above-described hardness tester, in which the first field lens is a lens having a magnification power of twenty times or greater, and the second field lens is a lens having a magnification power of five times or less.

Another aspect of the present invention is a hardness testing method of a hardness tester in which hardness of a specimen is measured by loading a predetermined testing force from an indenter on a surface of the specimen placed on a specimen stage to form an indentation, then measuring dimensions of the indentation. The hardness testing method includes a focusing process, a first image capturing process, a test position setting process, a focus position memory controlling process, an indentation creating process, a second image capturing process, and a measuring process. The focusing process positions a first field lens above the specimen, then focuses on the surface of the specimen by changing a relative distance between the specimen stage and the first field lens. The first image capturing process positions a second field lens having a magnification power less than the first field lens above the specimen, then captures an image of the surface of the specimen with an image capturer. The test position setting process sets the test position in which the indentation will be formed based on image information of the surface of the specimen captured in the first image capturing process. The focus position memory controlling process positions the first field lens above the specimen, then measures a focus position at a predetermined test position among the test positions set with the test position setting process. The focus position memory controlling process then associates the measured focus position with the test position within a predetermined range and stores the information in a memory. The indentation creating process positions the indenter above the specimen and forms the indentation in the test position. The second image capturing process positions the first field lens above the specimen, then obtains the focus position associated with the test position from the memory and displaces the specimen based on the obtained focus position and the test position. Thereafter, the second image capturing process captures an image of the indentation formed in the indentation creating process with the image capturer. The measuring process measures the hardness of the specimen based on the indentation whose image was captured in the second image capturing process.

According to the present invention, height information (focus position) corresponding to the test position can be obtained at a step before the indentation is formed. The specimen can also be positioned at an appropriate height without performing an autofocus process at the time of indentation creation and at the time of indentation scanning. Therefore, execution time for hardness testing can be shortened, and also no negative circumstance arises in which measurement errors are produced during indentation scanning. In addition, when the broad range image of the specimen is obtained, the low power second field lens can be used; thus, there is no need to obtain a large number of images, as compared to a case where the high power first field lens is used, and execution time for hardness testing can be shortened.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

Hereinafter, an embodiment of the present invention will be described with reference to the drawings. Furthermore, in the following description, the X direction in FIG. 1 will be the left-right direction, the Y direction will be the front-back direction, and the Z direction will be the up-down direction. Also, the X-Y plane will be the horizontal plane.

Figure 1:
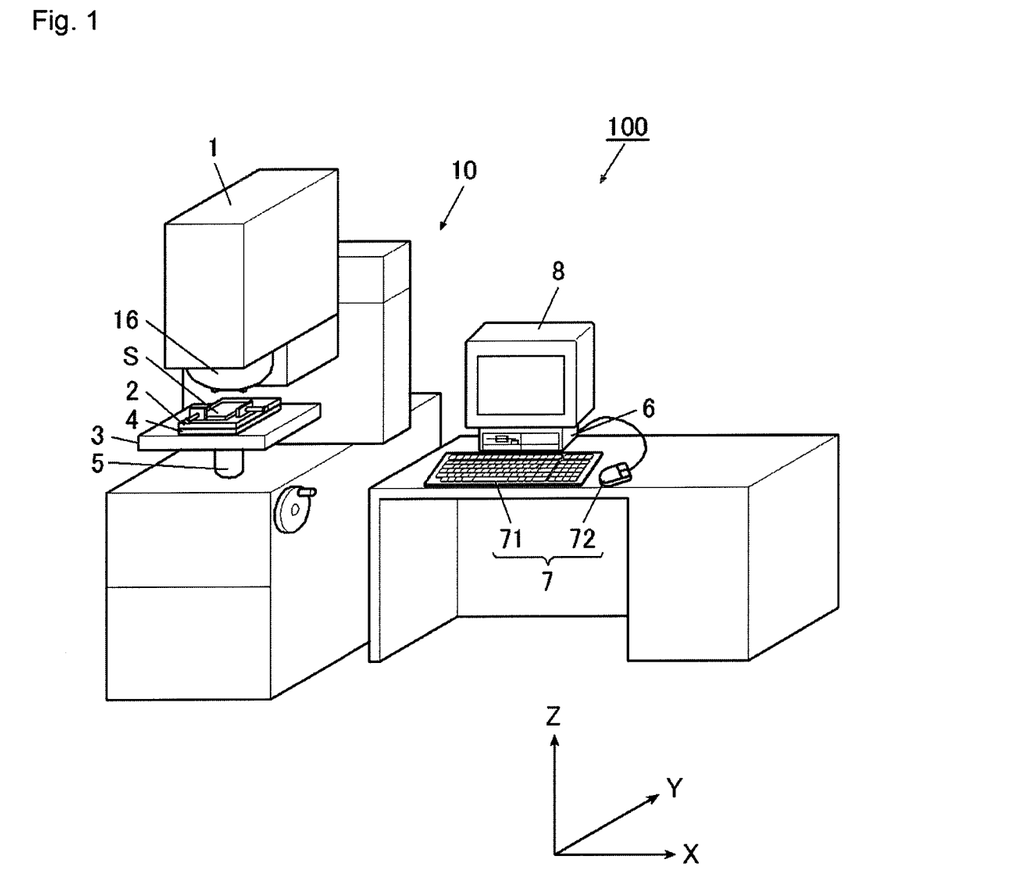
FIG. 1 is a perspective view of an overall configuration of a hardness tester according to the present invention.
Figure 2:
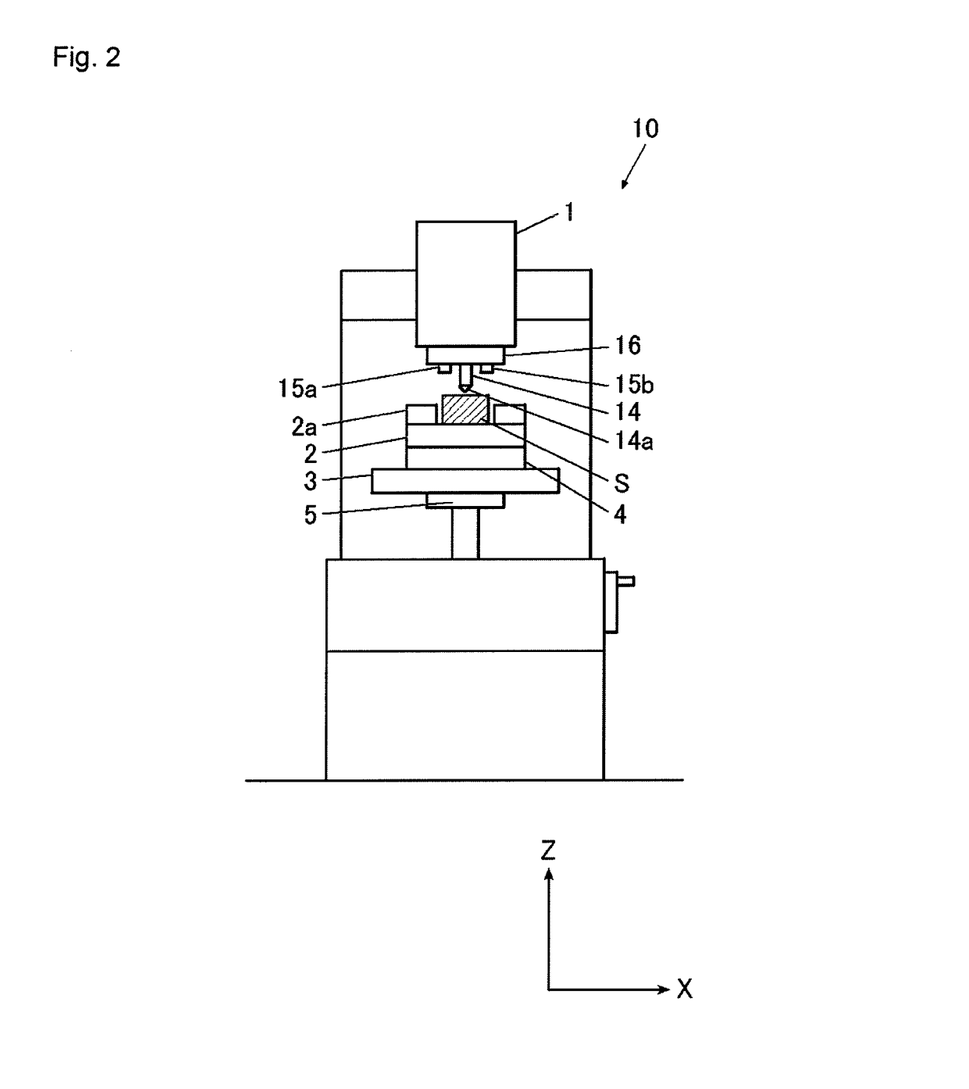
FIG. 2 is a schematic diagram illustrating a tester main body of the hardness tester according to the present invention.

A hardness tester 100 is, for example, a Vickers hardness tester and includes, as shown in FIGS. 1 and 2, a tester main body 10, a controller 6, an operator 7, and a monitor 8.

The tester main body 10 includes a hardness measurer 1, a specimen stage 2, an XY stage 3, an AF stage 4, and a lifting mechanism 5. The hardness measurer 1 performs hardness measurements on a specimen S. The specimen S is placed on the specimen stage 2. The XY stage 3 displaces the specimen stage 2. The AF stage 4 enables focusing on a surface of the specimen S. The lifting mechanism 5 raises and lowers the specimen stage 2 (the XY stage 3 and AF stage 4).

Figure 3:
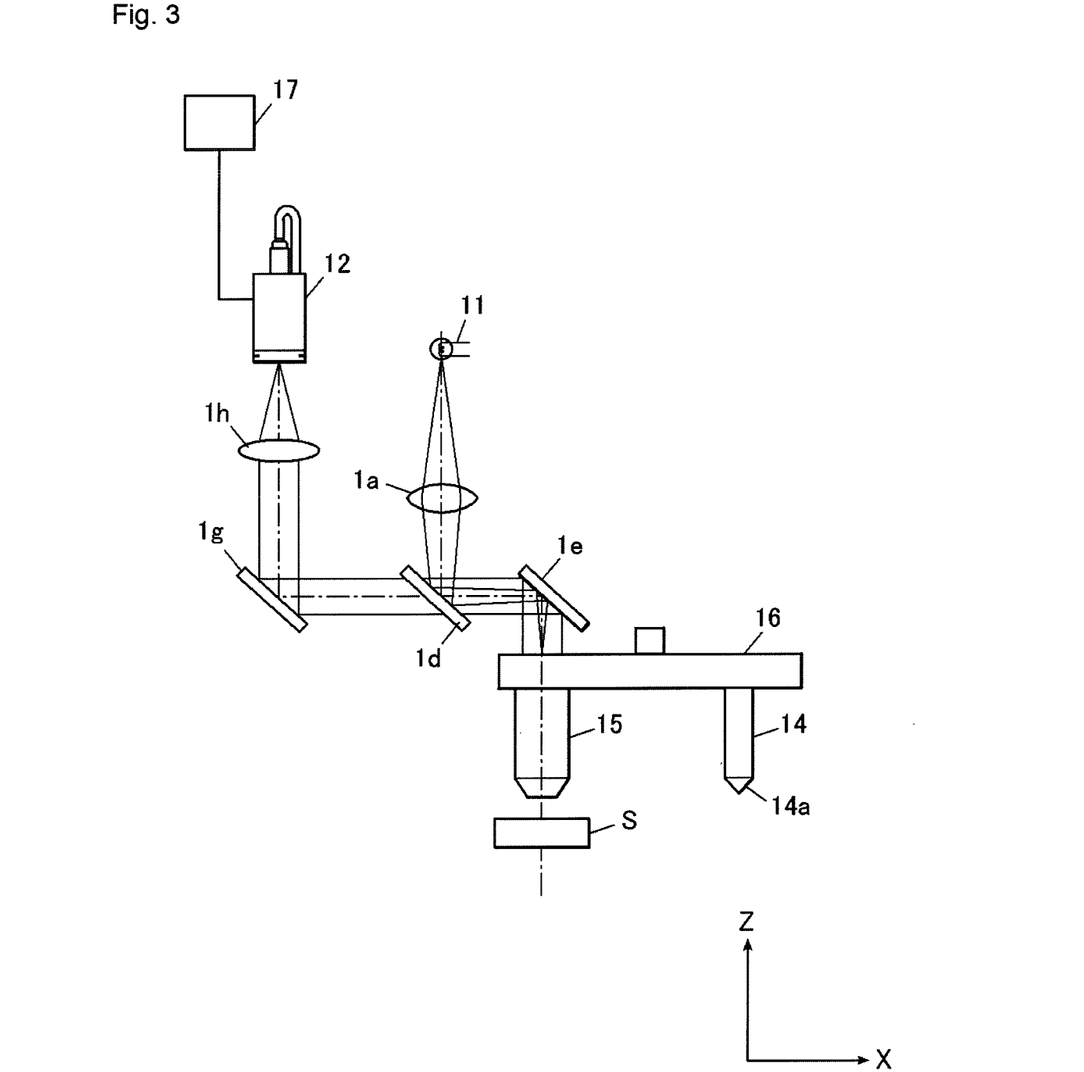
FIG. 3 is a schematic diagram illustrating a hardness measurer of the hardness tester according to the present invention.

The hardness measurer 1, for example and as shown in FIG. 3, includes an illumination device 11, a CCD camera 12, an indenter shaft 14 provided with an indenter 14a, and field lenses 15. The illumination device 11 illuminates the surface of the specimen S. The CCD camera 12 captures an image of the surface of the specimen S. The hardness measurer 1 is further configured with a turret 16, on which the indenter shaft 14 and the field lenses 15 may be swapped by rotation.

The illumination device 11 illuminates the surface of the specimen S by irradiating light thereon. The light irradiated from the illumination device 11 reaches the surface of the specimen S via a lens 1a, a half mirror 1d, a mirror 1e, and the field lenses 15.

Figure 4:
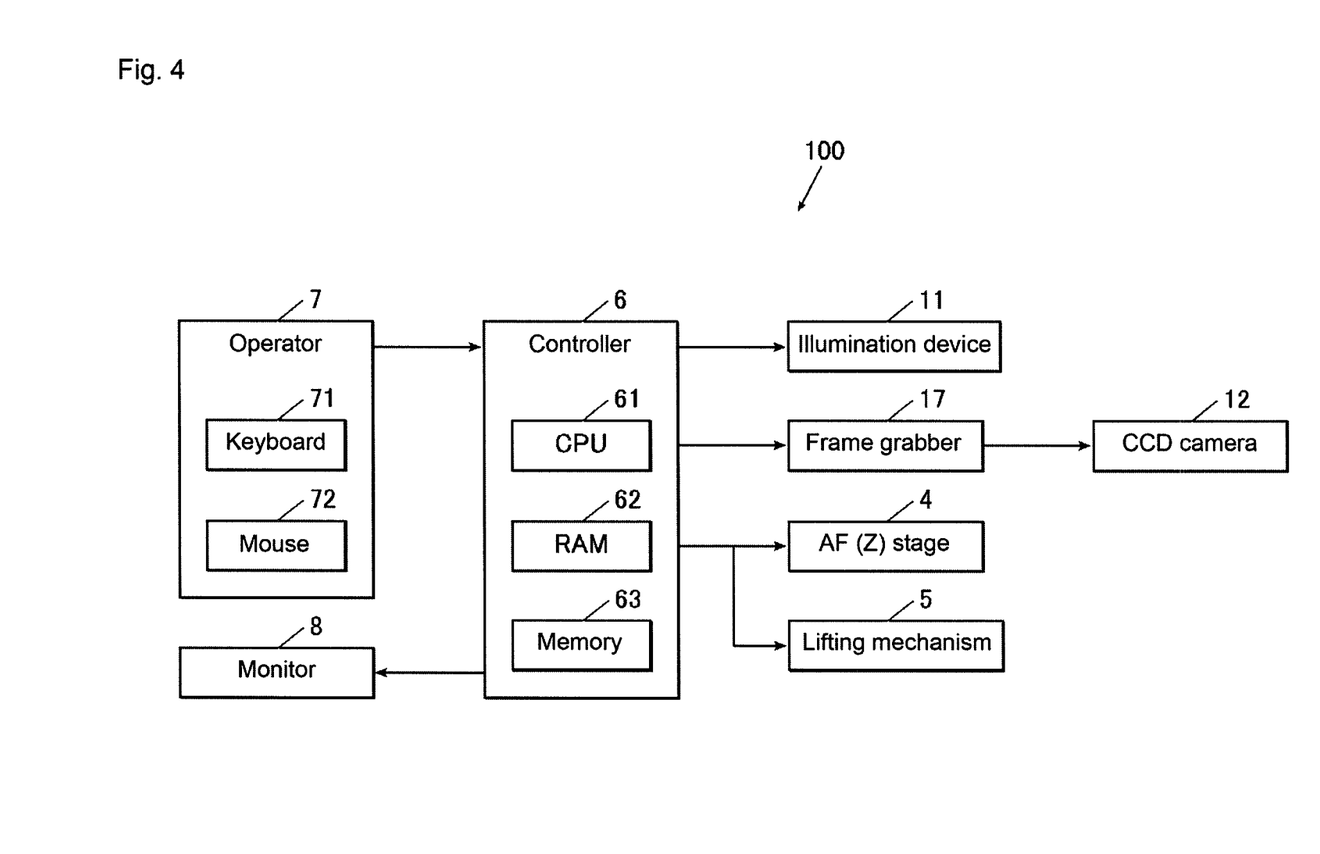
FIG. 4 is block diagram illustrating a control structure of the hardness tester according to the present invention.

The CCD camera 12, for example and as shown in FIGS. 3 and 4, captures an image of the surface of the specimen S and of the indentation formed thereon by the indenter 14a to obtain image data, based on reflected light input from the surface of the specimen S via the field lenses 15, the mirror 1e, the half mirror 1d, a mirror 1g, and a lens 1h. The CCD camera 12 then outputs the image data to the controller 6 via a frame grabber 17 which is able to simultaneously accumulate and store image data for a plurality of frames. Accordingly, the CCD camera 12 acts as the image capturer.

The indenter shaft 14 is displaced toward the specimen S resting on the specimen stage 2 and the indenter 14a provided to the tip thereof is pressed onto the surface of the specimen S with a predetermined testing force by a load mechanism (not shown in the drawings) driven according to a control signal output by the controller 6.

The field lenses 15 are collective lenses configured with differing powers of magnification and are plurally supported on a bottom face of the turret 16. The field lenses 15 are placed above the specimen S by rotation of the turret 16, and thereby uniformly irradiate light irradiated from the illumination device 11 onto the surface of the specimen S. Specifically, the field lenses 15 include a high power field lens (first field lens) 15a and a low power field lens (second field lens) 15b having a magnification power less than the high power field lens 15a. The high power field lens 15a, specifically, is preferably a lens having a magnification power of twenty times or greater. When the magnification power is twenty times or greater, field depth is shallow and does not exceed an allowed range for height of the specimen S during indentation. Therefore, positioning accuracy for the height of the specimen S can be increased. Meanwhile, the low power field lens 15b, specifically, is preferably a lens having a magnification power of five times or less. When the magnification power is five times or less, an image having a high field of view can be obtained. Therefore, the broad range image G1 can be easily obtained.

The indenter shaft 14 and the plurality of field lenses 15 (the high power field lens 15a and the low power field lens 15b) are mounted to the bottom face of the turret 16. The turret 16 is configured to enable switching between the indenter shaft 14 and one of the field lenses 15 to position the same above the specimen S by rotating the turret 16 around the Z-axis direction. In other words, by positioning the indenter shaft 14 above the specimen S, the indentation can be formed in the surface of the specimen S, and by positioning the field lenses 15 above the specimen S, the formed indentation can be observed.

The specimen stage 2 fixes the specimen S, resting on an upper surface thereof, in place with a specimen holder 2a. The XY stage 3 is driven by a drive mechanism (not shown in the drawings) in response to a control signal output by the controller 6. The XY stage 3 then displaces the specimen stage 2 in a direction (X-axis and Y-axis directions) perpendicular to a displacement direction (Z-axis direction) of the indenter 14a. The AF stage 4 is driven in response to a control signal output by the controller 6. The AF stage 4 then minutely raises and lowers the specimen stage 2 based on image data captured by the CCD camera 12 in order to focus on the surface of the specimen S. The lifting mechanism 5 is driven in response to a control signal output by the controller 6. By displacing the specimen stage 2 (the XY stage 3 and the AF stage 4) in the up-down direction, the lifting mechanism 5 changes the relative distance between the specimen stage 2 and the field lenses 15. The focuser is configured with the lifting mechanism 5 and the AF stage 4.

The operator 7 is configured with a keyboard 71 and a mouse 72, and executes an input operation from the user when hardness testing is performed. Also, when a predetermined input operation is performed by the operator 7, a predetermined operation signal corresponding to the input operation is output to the controller 6.

Specifically, the operator 7 enables the user to select conditions determining a focus position for the indentation via the keyboard 71, the mouse 72, and the like. Further, the operator 7 can designate a range in which the specimen stage 2 (the lifting mechanism 5 and the AF stage 4) is displaced (a range of relative distance between the specimen stage 2 and the field lenses 15). The operator 7 also enables the user to input test condition values from a point when a hardness test is being executed by the hardness tester 100. The input test condition values are transmitted to the controller 6. Herein, test condition values are, for example, material of the specimen S, test force (N) loaded onto the specimen S by the indenter 14a, magnification power of the field lenses 15, and the like. The operator 7 also enables the user to select either of a manual mode in which determination of focus positions for the indentation is performed manually and an automatic mode in which the determination is performed automatically.

The monitor 8 is, for example, configured with a display apparatus such as an LCD, and displays programmed conditions for a hardness test input with the operator 7, results of the hardness test, images of the surface of the specimen S and the indentation formed thereon captured by the CCD camera 12, and the like.

As shown in FIG. 4, the controller 6 includes a CPU (Central Processing Unit) 61, a RAM (Random Access Memory) 62, and a memory 63. By executing a predetermined program stored in the memory 63, the controller 6 performs operation control for the performance of a predetermined hardness test, and the like.

The CPU 61 reads a processing program stored in the memory 63, then moves the program to the RAM 62 for execution. Thereby, the CPU 61 performs control on the entire hardness tester 100.

The RAM 62 moves the processing program executed by the CPU 61 to a program storage region within the RAM 62. In addition, the RAM 62 stores input data, processing results generated when the processing program is executed, and the like in a data storage region.

The memory 63 includes, for example, a memory medium (not shown in the drawings) storing programs, data, and the like. The memory medium is configured with a semiconductor memory and the like. Further, the memory 63 stores various kinds of data for implementing an operation in which the CPU 61 controls the entire hardness tester 100, various kinds of processing programs, data processed by the execution of these programs, and the like. More specifically, the memory 63 stores, for example, an XY stage control program, an autofocus program, a hardness measurer control program, and the like.

By executing the XY stage control program stored in the memory 63, the CPU 61 displaces the XY stage 3 so as to position a predetermined region on the surface of the specimen S directly below the CCD camera 12. By executing the autofocus program stored in the memory 63, the CPU 61 also raises and lowers the AF stage 4 to perform autofocus with respect to the surface of the specimen S based on image information obtained by the CCD camera 12 of the hardness measurer 1. By executing the hardness measurer control program stored in the memory 63, the CPU 61 also presses the indenter 14a onto the surface of the specimen S with a predetermined test force to form the indentation, measures the length of diagonal lines in the indentation based on image information for the surface of the specimen S generated by the CCD camera 12, and the like. In addition, the CPU 61 calculates the hardness of the specimen S based on the measured length of the diagonal lines in the indentation. The CPU 61 also displays on the monitor 8 image information for the surface of the specimen S generated by the CCD camera 12, calculation results for the hardness of the specimen S calculated by execution of the hardness measurer control program, and the like.

Next, the operation of the hardness tester 100 according to the present embodiment is described with reference to the flowchart of FIG. 5. This process is implemented by the CPU 61 executing a program stored in the memory 63.

First, the CPU 61 focuses on the surface of the specimen S using the high power field lens 15a (step S1: focusing process). Specifically, based on image data captured by the CCD camera 12 through the high power field lens 15a, the lifting mechanism 5 and the AF stage 4 (focuser) are controlled to minutely raise and lower the specimen stage 2. Autofocus is then performed with respect to a desired position on the surface of the specimen S, and positioning for the height of the specimen S is performed.

Next, the CPU 61 obtains the broad range image G1 of the specimen S using the low power field lens 15b (step 2: first image capturing process). Specifically, as shown in FIG. 6, a plurality of images A1-A9 are combined to obtain the broad range image G1, the images A1-A9 obtained by displacing the specimen S in the horizontal direction and capturing the images with the CCD camera 12 through the low power field lens 15b.

Next, the CPU 61 sets a test pattern for the obtained broad range image G1 (step S3: test position setting process). Herein, the setting of the test pattern means setting test conditions (e.g., material of the specimen S, test force (N) loaded on the specimen S by the indenter 14a, magnification power of the field lenses 15, and the like), a test start point, number of rows and columns, pitch, and the like. By setting the test pattern, as shown in FIG. 6, test positions P1, P2, . . . are programmed. In other words, based on the broad range image G1 of the surface of the specimen S captured by the CCD camera 12 through the low power field lens 15b, the CPU 61 acts as a test position setter setting the test positions P1, P2, . . . at which an indentation will be formed.

Figure 7:
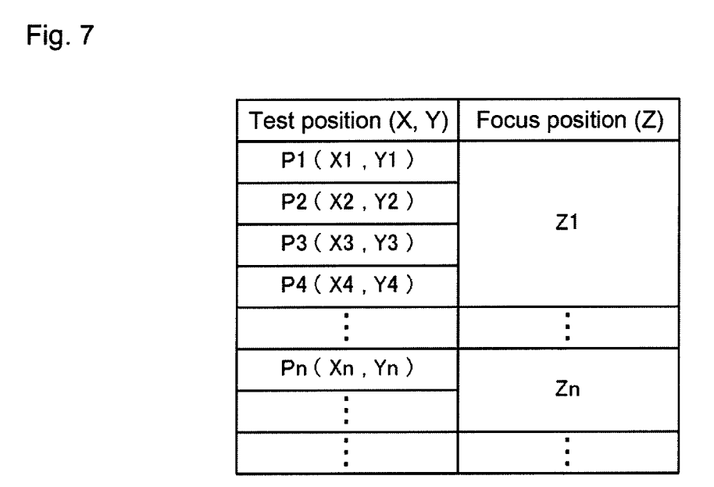
FIG. 7 illustrates an example where focus positions have been associated with test positions.

Next, the CPU 61 measures the focus position at a predetermined test position using the high power field lens 15a, then converts the measurement results into a database and stores the results in the memory 63 (step S4: focus position memory controlling process). Specifically, one point (or a plurality of points) is picked out for each predetermined range within the test positions set in step S3, then autofocus is performed at the picked-out test position. The height of the specimen S when in focus is measured as the focus position, and the measured focus position is associated with a test position within the predetermined range and stored in the memory 63. For example, as shown in FIG. 7, one point (for example, test position P1) is picked out in a predetermined range (for example, a range that includes test positions P1-P4). A focus position Z1 for the picked-out test point P1 is then associated with the test positions P1-P4 within the predetermined range and stored in the memory 63. That is, the CPU 61 measures through the high power field lens 15a the focus position at the predetermined test position from among the test positions set in step S3. The CPU 61 then associates the measured focus position with the test position within the predetermined range and stores the information in the memory 63. The CPU 61 thus acts as the focus position memory. Herein, the reason for picking out one point (or a plurality of points) for each predetermined range is because there is no need to measure focus positions for all test positions within the predetermined range for a predetermined range (i.e., a range in which no substantive difference is observed in focus positions for each test position). Another reason for picking out one point (or a plurality of points) for each predetermined range is because, by thinning out the measurements for focus positions as described above, the execution time for the hardness test can be shortened.

Next, the CPU 61 displaces the specimen S (specimen stage 2) so as to position the predetermined test position (in the first cycle, the test start point) opposite the indenter 14a (step S5). Because the focus position corresponding to the test position has been measured in step S4, the height of the specimen S is displaced to the focus position. Also, the CPU 61 forms the indentation at the test position with the indenter 14a (step S6: indentation creating process). In other words, the CPU 61 acts as the indentation creator forming the indentation at the test position with the indenter 14a.

Next, the CPU 61 determines whether or not an indentation has been created for all of the measured test positions (step S7). When an indentation has not been created for all of the test positions (that is, when the CPU 61 determines that at least one test position has not had an indentation created threat) (step S7: NO), the CPU 61 moves to step S5 and displaces the specimen S so as to position the next test position opposite the indenter 14a. Meanwhile, when the CPU 61 determines that indentation has been performed for all of the test positions (step S7: YES), the CPU 61 moves to the next step, step S8.

Next, the CPU 61 displaces the specimen S so as to position the predetermined scanning position (position where indentation has been performed) opposite the high power field lens 15a used for indentation scanning (step S8). Because the focus position corresponding to the scanning position has been measured in step S4, the focus position is obtained from the memory 63 and the height of the specimen S is displaced to the focus position.

Next, the CPU 61 scans the indentation at the scanning position, then calculates a hardness value for the specimen S based on the scanned dimensions of the indentation (step S9: second image capturing process, measuring process). Specifically, an image of the indentation is captured by the CCD camera 12 through the high power field lens 15a, then the length of diagonal lines in the indentation is measured based on the captured image data of the indentation. The hardness value for the specimen S is then calculated based on the length of the diagonal lines. That is, after displacing the specimen S based on the scanning position (test position and focus position), the CPU 61 acts as the image capture controller capturing an image of the indentation formed in step S6 with the CCD camera 12 through the high power field lens 15a. The CPU 61 also acts as the measurer measuring the hardness of the specimen based on the indentation whose image was captured in step S9.

Next, the CPU 61 determines whether or not the indentation has been scanned at all scanning positions (step S10). When the CPU 61 determines that the indentation has not been scanned at all scanning positions (that is, when the CPU 61 determines that the indentation has not been scanned at at least one scanning position) (step S10: NO), the CPU 61 moves to step S8 and displaces the specimen S so as to position the next scanning position opposite the indenter 14a. Meanwhile, when the CPU 61 determines that the indentation has been scanned at all scanning positions (step S10: YES), the CPU 61 ends the process.

As in the above, the hardness tester 100 according to the present embodiment includes the focuser (the lifting mechanism 5 and the AF stage 4), the CCD camera 12, the test position setter (the CPU 61), the focus position memory (CPU 61), the indentation creator (CPU 61), the image capture controller (CPU 61), and the measurer (CPU 61). The focuser (lifting mechanism 5 and AF stage 4) focuses on the surface of the specimen S by changing the relative distance between the specimen stage 2 and one of the high power field lens 15a and the low power field lens 15b having a magnification power less than the high power field lens 15a. The CCD camera 12 captures an image of the surface of the specimen S through one of the high power field lens 15a and the low power field lens 15b. The test position setter (the CPU 61) sets the test positions P1, P2, . . . at which the indentation will be formed based on image information (the broad range image G1) for the surface of the specimen S captured by the CCD camera 12 through the low power field lens 15b. The focus position memory (CPU 61) measures a focus position through the high power field lens 15a at a predetermined test position among the test positions P1, P2, . . . set by the test position setter, then associates the measured focus position with the test position within the predetermined range and stores the information in the memory 63. The indentation creator (CPU 61) forms the indentation at the test positions P1, P2, . . . with the indenter 14a. The image capture controller (CPU 61) obtains the focus positions associated with the test positions P1, P2, . . . from the memory 63, then displaces the specimen S based on the obtained focus positions and test positions P1, P2, . . . . Thereafter, the image capture controller (CPU 61) captures an image of the indentation formed by the indentation creator with the CCD camera 12 through the high power field lens 15a. The measurer (CPU 61) measures the hardness of the specimen S based on the indentation whose image has been captured by the control of the image capture controller. For this reason, height information (focus position) corresponding to a test position can be obtained at a stage before the indentation is formed. For this reason also, the specimen S can be positioned at an appropriate height without performing an autofocus process at the time of indentation creation and at the time of indentation scanning. Thus, execution time for the hardness test can be shortened and, in addition, a negative circumstance does not arise in which measurement errors are produced during indentation scanning. Further, when obtaining the broad range image G1 of the specimen S, the low power field lens 15b having a high field of view can be used. Thus, there is no need to obtain a large number of images, and execution time for the hardness test can be shortened.

With the hardness tester 100 according to the present embodiment, the high power field lens 15a is a lens having a magnification power of twenty times or greater. Thus, the field depth is shallow and does not exceed the allowed range for height of the specimen S during indentation creation. Positioning accuracy for the height of the specimen S can also be improved. The low power field lens 15b is a lens having a magnification power of five times or less. Thus, images having a high field of view can be obtained, and the broad range image G1 can be easily obtained.

Above, a specific description was given based on an embodiment according to the present invention. However, the present invention is not limited to the above-described embodiment and modifications are possible within a scope not deviating from the substance of the present invention.

Figure 5:
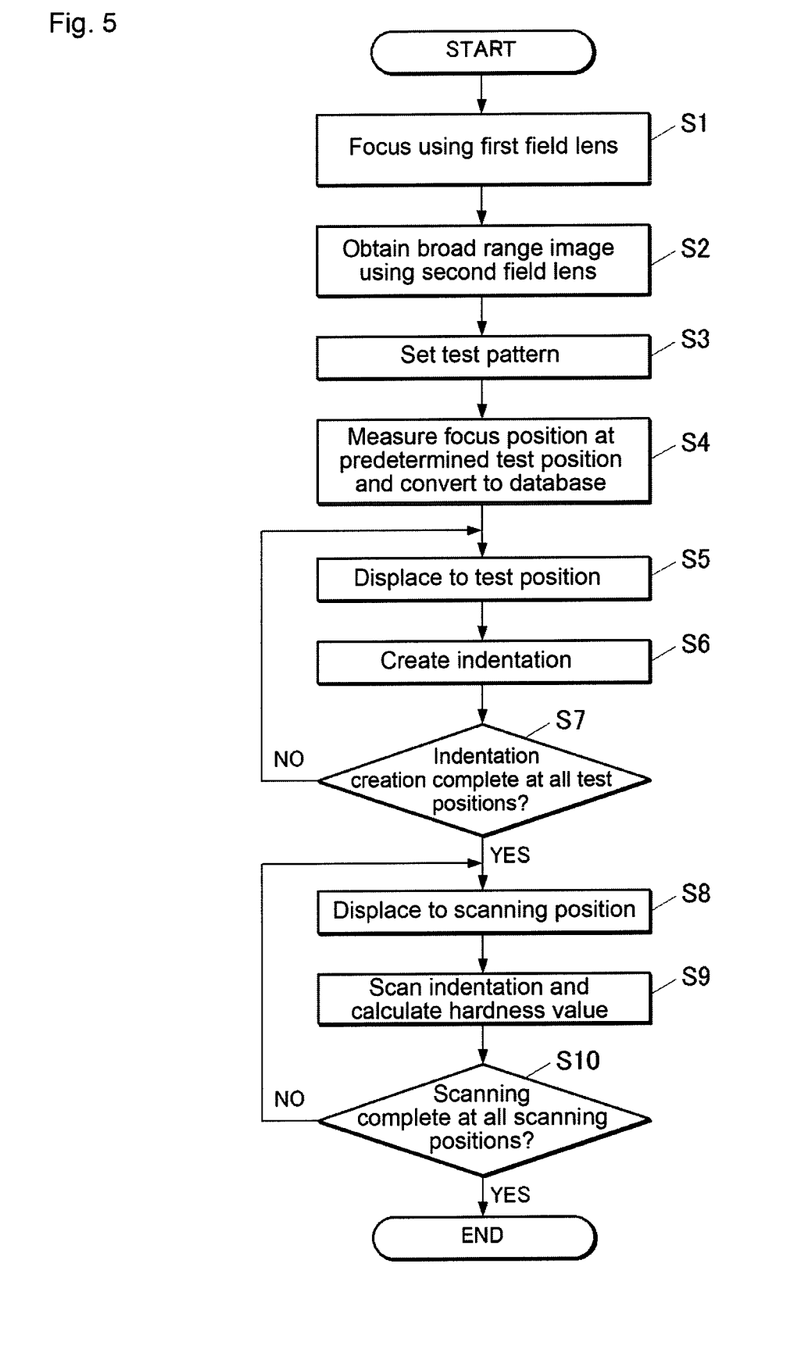
FIG. 5 is a flowchart illustrating an operation of the hardness tester according to the present invention.

For example, in the above-described embodiment, in step S8 shown in FIG. 5, the specimen S is displaced so as to position the predetermined scanning position opposite the high power field lens 15a, then the height of the specimen S is displaced to the focus position. Thereafter, without performing an autofocus process, an indentation scanning operation is performed. However, the present invention is not limited to this. In the above-described embodiment, focus positions are not measured at every test position. Therefore, even when the height of the specimen S is displaced to the focus position, there is a possibility that the degree of focus will be low for certain test positions. Imagining such a case, the degree of focus may be calculated during indentation scanning and, when the degree of focus is determined to be low, an autofocus process may also be performed.

In addition, in the above-described embodiment, an example was described including two field lenses 15 (the high power field lens 15a and the low power field lens 15b). However, the present embodiment is not limited to this. So long as the present invention includes at least two field lenses 15 of different magnification powers, mid-power field lenses may also be added, for example, to the high power field lens 15a and the low power field lens 15b.

Besides the above, modifications are possible as appropriate within the scope of the present invention's description, even as related to details of structure and operation for each component configuring the hardness tester 100.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester for measuring hardness of a specimen by loading a predetermined testing force from an indenter on a surface of a specimen placed on a specimen stage to form an indentation, then measuring dimensions of the indentation, the hardness tester comprising:
- a focuser configured to focus on the surface of the specimen by changing a relative distance between a specimen stage and one of a first field lens and a second field lens having a magnification power less than the first field lens;
- an image capturer capturing an image of the surface of the specimen through one of the first field lens and the second field lens;
- a test position setter configured to set a test position at which the indentation is formed based on image information for the surface of the specimen captured by the image capturer through the second field lens;
- a focus position memory controller configured to measure a focus position through the first field lens at a predetermined test position among the test positions set by the test position setter, then associating the measured focus position with a test position within a predetermined range and storing the information in a memory;
- an indentation creator configured to form the indentation at the test position with the indenter;
- an image capture controller configured to obtain the focus position associated with the test position from the memory, displace the specimen based on the obtained focus position and the test position, and thereafter capture an image of the indentation formed by the indentation creator with the image capturer through the first field lens; and
- a measurer configured to measure the hardness of the specimen based on the indentation whose image has been captured by the control of the image capture controller.

2. The hardness tester according to claim 1, wherein the first field lens is a lens having a magnification power of twenty times or greater, and the second field lens is a lens having a magnification power of five times or less.

3. A hardness testing method of a hardness tester, wherein hardness of a specimen is measured by loading a predetermined testing force from an indenter on a surface of the specimen placed on a specimen stage to form an indentation, then measuring dimensions of the indentation, the method comprising:
- positioning a first field lens above the specimen, then focusing on the surface of the specimen by changing a relative distance between the specimen stage and the first field lens;
- positioning a second field lens having a magnification power less than the first field lens above the specimen, then capturing an image of the surface of the specimen with an image capturer;
- setting the test position in which the indentation is formed based on image information of the surface of the specimen captured in said positioning of the second field lens;
- positioning the first field lens above the specimen, measuring a focus position at a predetermined test position among the test positions set with said setting of the test position in which the indentation is formed, then associating the measured focus position with the test position within a predetermined range and storing the information in a memory;
- positioning the indenter above the specimen and forming the indentation in the test position;
- again positioning the first field lens above the specimen, obtaining the focus position associated with the test position from the memory and displacing the specimen based on the obtained focus position and the test position, and thereafter capturing with the image capturer, an image of the indentation formed in said positioning of the indenter; and
- measuring the hardness of the specimen based on the indentation whose image was captured in said again positioning of the first field lens above the specimen.

* * * * *